United States Patent [19]

Nitecki

[11] Patent Number: 5,281,698
[45] Date of Patent: Jan. 25, 1994

[54] PREPARATION OF AN ACTIVATED POLYMER ESTER FOR PROTEIN CONJUGATION

[75] Inventor: Danute E. Nitecki, Berkeley, Calif.

[73] Assignee: Cetus Oncology Corporation, Emeryville, Calif.

[21] Appl. No.: 734,749

[22] Filed: Jul. 23, 1991

[51] Int. Cl.$^5$ .................. C07D 207/404; C07K 3/08; C07K 15/06; C07K 15/26
[52] U.S. Cl. .................. 530/351; 530/405; 530/409; 548/520; 548/545; 548/547
[58] Field of Search .......... 530/409, 405, 351; 548/520, 545, 546, 547

[56] References Cited

U.S. PATENT DOCUMENTS

| | | | |
|---|---|---|---|
| 4,341,707 | 7/1982 | Ogura et al. | 530/335 |
| 4,904,584 | 2/1990 | Shaw | 514/8 |
| 5,235,028 | 8/1993 | Barany et al. | 530/334 |

OTHER PUBLICATIONS

*Polymer Preprints*, vol. 31, No. 2, Aug. 1990, pp. 173-174 and 213-214.

Primary Examiner—Jeffrey E. Russel
Attorney, Agent, or Firm—Grant D. Green; Kenneth M. Goldman; Philip L. McGarrigle, Jr.

[57] ABSTRACT

The present invention is a process for preparing an activated ester of polyethylene glycol or a polyoxyethylated polyol. After the activated ester is prepared, it can be reacted with a protein to form a polymer/protein conjugate. Conjugation with a polymer can reduce the protein's immunogenicity, increase its solubility, and increase its circulating in vivo half-life. Preferred proteins are IL-2, CSFs, and interferons.

20 Claims, 2 Drawing Sheets

PREPARATION OF AN ACTIVATED POLYMER ESTER FOR PROTEIN CONJUGATION

FIELD OF THE INVENTION

The present invention describes a method for preparing an activated polymer ester. Once the activated polymer ester is formed it can be used to chemically modify a protein.

BACKGROUND OF THE INVENTION

Various natural and recombinant proteins have medical and pharmaceutical utility. Once they have been purified, separated, and formulated, they can be parenterally administered to disadvantaged hosts. However, parenterally administered proteins may stimulate an immune response, may be relatively water insoluble, and may have suboptimal pharmokinetic behavior. Consequently, it can be difficult to achieve therapeutically useful blood levels in patients.

These problems may be overcome by conjugating the proteins to polymers. For example, polyethylene glycol (PEG) can be conjugated to proteins for various purposes. Davis et al. U.S. Pat. No. 4,179,337 discloses conjugating polyethylene glycol to polypeptides, such as enzymes and insulin. Davis et al. made these conjugates so that the protein would be less immunogenic and would retain a substantial proportion of its physiological activity. Davis et al. also disclose methods for placing a reactive group on PEG and subsequently conjugating it to a protein. Iwashita et al. U.S. Pat. No. 4,412,989, disclose covalently conjugating polyethylene glycol to an oxygen carrying molecule. This conjugate is useful as a blood substitute. Veronese et al., *Applied Biochem. and Biotech.*, 11: 141-152 (1985) disclose activating polyethylene glycols with phenyl chlorofonnates to modify a ribonuclease and a superoxide dismutase. Katre et al. U.S. Pat. No. 4,766,106 also disclose solubilizing proteins by polymer conjugation. For example, PEG, and other polymers, are conjugated to recombinant proteins to reduce immunogenicity and increase in vivo blood levels, among other things. These compounds may more specifically include interleuldn-2 (IL-2), interferon-$\beta$ (IFN-$\beta$), immunotoxins, and other proteins that share similar characteristics. Nishimura et al., European Patent Application 154,316 and Tomasi International Application Number PCT/US85/02572, disclose similar subject matter.

The process for attaching PEG to these useful recombinant proteins is important. Accordingly, the present invention is an advantageous modification in the process for preparing a PEG active ester.

SUMMARY OF THE INVENTION

The present invention is an activated polymer for attachment to a protein. More specifically, the present invention is a method for producing an activated ester of polyethylene glycol (PEG) or a polyoxyethylated polyol, comprising contacting a PEG or a polyoxyethylated polyol, which has at least one hydroxyl group, with disuccinimidylcarbonate (DSC) under the appropriate reaction conditions to form a PEG or a polyoxyethylated polyol active ester.

Among other factors, it has been discovered that the present method can produce an active PEG ester (see FIG. 2) that will react with proteins to yield a stable urethane linkage between the polymer and the protein. The present activated ester reacts quicker with the substrate protein than another derivative which also yields stable urethane linkage. Additionally, using DSC is more advantageous than prior art methods for producing the active ester of FIG. 2. These earlier methods to produce the same ester are disadvantageous because they use unstable reactants (chlorocarbonates of N-hydroxysuccimide) and involve use of phosgene at the reaction site, which is quite disadvantageous.

DETAILED DESCRIPTION OF THE INVENTION

Figure 1:
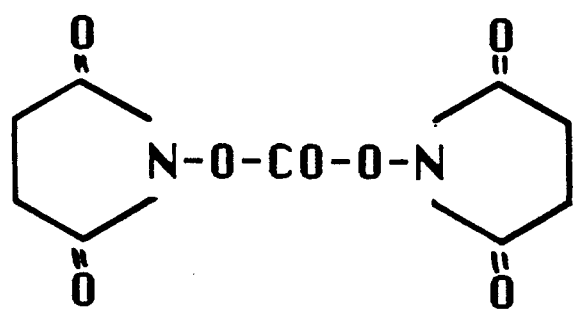
FIG. 1 shows the chemical structure of DSC.

As mentioned above, the present invention is a process designed to produce an activated polymer for conjugation to a protein. This process can stably solubilize, reduce the immunogenicity, and increase the circulating half-life of proteins.

Polymers:

In a specific embodiment of the present invention, a purified protein is covalently conjugated to a homopolymer of polyethylene glycol (PEG) or a polyoxyethylated polyol (POP). PEG is soluble in water at room temperature and has the general formula: $R(O-CH_2-CH_2)_nO-R$ where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1000 and 40,000, more preferably between 2000 and 20,000, most preferably between 3,000 and 12,000. Preferably, PEG has at least one hydroxy group, more preferably it is a terminal hydroxy group. It is this hydroxy group which is preferably activated to react with a free amino group on the protein. However, it will be understood that the type and amount of the reactive groups may be varied to achieve a covalently conjugated PEG/protein of the present invention.

Water soluble polyoxyethylated polyols are all useful in the present invention. They include polyoxyethylated sorbitol, polyoxyethylated glucose, polyoxyethylated glycerol (POG), etc. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG. The structure for POG is shown in Knauf et al. *J. Bio. Chem.*, 263:15064-15070(1988) and a discussion of POG/EL-2 conjugates is found in U.S. Pat. No. 4,766,106, both of which are hereby incorporated by reference in their entireties.

The following discussion is directed to the conjugation of these water soluble polymers to IL-2 as a representative protein. It should be understood that even though PEG or POG is mentioned, the other recited water soluble polymers can be used. Furthermore, it should be understood that other proteins besides IL-2 can be conjugated to the water soluble polymer. For example, proteins which have free amino groups can be conjugated. Other examples of representative proteins include colony stimulating factors and interferons. It should be understood that the discussion of the specific proteins can also apply to other proteins as the techniques to produce and purify the proteins can be generally similar.

The PEG or POG is attached to the protein by covalent conjugation. "Covalently conjugated" or "conjugated" refer to the attachment of PEG or POG to a protein via an activated PEG or POG. "Active" or "activated" describes the attachment of a reactive group onto a PEG or POG hydroxyl (—OH) group, so that they can be conjugated to the protein. Generally, the PEG or POG molecule is activated by attaching the reactive group to a hydroxyl group and then the active molecule is covalently conjugated to an amino group on the protein. While conjugation may occur between any reactive amino acids on the protein, the reactive amino acid is preferably lysine. The lysine is linked to a reactive group on PEG or POG through its free $\epsilon$-amino group.

Proteins:

As stated above, PEG or POG is attached to IL-2 as an example of a protein. Interleukin-2 (IL-2) is a lymphokine which is produced by normal peripheral blood lymphocytes and is present in the body at low concentrations. It induces the proliferation of antigen or mitogen stimulated T cells after exposure to plant lectins, antigens, or other stimuli. IL-2 was first described by Morgan, D. A., et al., *Science* (1976) 193:1007–1008 and originally called T cell growth factor because of its ability to induce proliferation of stimulated T lymphocytes. It is a glyco-protein with a reported native molecular weight in the approximate range of 13,000 to 17,000 daltons (S. Gillis and J. Watson, *J. Exp. Med.*, 1980, 159:1709) and has an isoelectric point in the approximate range of 6–8.5. It is now recognized that in addition to its growth factor properties, it modulates various in vitro and in vivo functions of the immune system. IL-2 is one of several lymphocyte-produced messenger/regulatory molecules that mediate cellular interactions and functions.

Modifications to the primary structure itself, by deletion, addition, or alteration of the amino acids incorporated into the sequence during translation, can be made without destroying the activity of the protein. Such modified proteins, known as "muteins", are described in U.S. Pat. No. 4,518,584, issued May 21, 1985, and U.S. Pat. No. 4,752,585, issued Jun. 21, 1985, both are hereby incorporated by reference in their entireties. The precise chemical structure of IL-2 depends on a number of factors, such as pH, glycosylation, derivitization, and other modifications as shown in U.S. Pat. No. 4,902,502 which is hereby incorporated by reference in its entirety.

IL-2 can be produced by a prokaryotic microorganism or a eukaryodc cell that has been transformed with a native or modified human IL-2 DNA sequence. Preferably, the IL-2 is produced by transforming a prokaryotic microorganism with DNA to produce a protein that possesses native human IL-2 activity. It is unglycosylated when produced in *E. coli*. Bacteria are preferred prokaryotic microorganisms for producing IL-2 and *E. coli* is especially preferred. For examples of bacterial production of IL-2 see: U.S. Pat. Nos. 4,518,584, 4,752,585, 4,738,927, and 4,564,593 which are all hereby incorporated by reference in their entireties. A typical transformed microorganism useful in the present invention is *E. coli* K-12, strain MM294, transformed with plasmed pLW1 (deposited at the American Type Culture Collection on Aug. 4, 1983 by Cetus Corporation under the provisions of the Budapest Treaty and having accession No. 39,405). Synthetic recombinant IL-2 can also be made in eukaryotes, such as yeast or human cells.

Processes for growing, harvesting, disrupting, or extracting the IL-2 from cells are substantially described in U.S. Pat. Nos. 4,604,377; 4,738,927; 4,656,132; 4,569,790; 4,748,234; 4,530,787; 4,572,298; 4,518,584, 4,752,585, U.S. Ser. Nos. 167,144 (now abandoned); 48,408 (now abandoned) and 200,741 (now abandoned) which are hereby incorporated by reference in their entireties. Other procedures for purifying native IL-2 from T cells are described by Watson, J. et al., *J. Exp. Med.*, 1979, 150:849–861; Gillis, S., et al., *J. Immunology*, 1980, 124:1954–1962; Mochizuki, D. Y., et al., *J. Immun Meth.*, 1980, 39:185–201; Welte, K. et al., *J. Exp. Med.*, 1982, 156:454–464; and European Patent Applications 83103582.9 (published Oct. 26, 1983 under No. 92163) and 83400938.3(published Nov. 16, 1983 under No. 94317) which are also incorporated by reference in their entireties.

The present invention also includes the use of a colony stimulating factor (CSF). The term CSF is intended to include macrophage-CSF (M-CSF), granulocyte-CSF (G-CSF), granulocyte/macrophage-CSF (GM-CSF), and multi-CSF.

M-CSF is a protein which exhibits the spectrum of activity understood in the art for M-CSF also known as CSF-1, i.e., when applied to the standard in vitro colony stimulating assay of Metcalf, 1970, *J. Cell Physiol.*, 76:89 as modified by Ralph et al. supra, it is capable of stimulating the formation of primarily macrophage colonies. Native M-CSF is a glycosylated dimer, dimerization is reported to be necessary for activity as the monomer is not active in the Metcalf or Ralph colony stimulating assays or various other in vitro bioactivity assays (Das et al. 1981, *Blood* 58:630–641; Das et al., 1982, *J. Biol. Chem.*, 257:13679–13681; Stanley et al., 1977, *J. Biol. Chem.*, 252:4305–4312, Halenbeck et al., 1989, *Bio/Technology*, 7:710–715). The term "M-CSF" refers to proteins that have M-CSF activity in the assays described above and are substantially homologous to the native sequence. An example M-CSF sequence and a discussion of various deletion mutants is shown in U.S. Pat. No. 4,847,201; another M-CSF is reported in U.S. Pat. No. 4,879,227 both of which these patents are hereby incorporated by reference in their entireties.

M-CSF apparently occurs in numerous forms all which are included in the embodiments of the present invention. Human M-CSF cDNA clones coding for M-CSF proteins of three different lengths ($\alpha$, 256 amino acids; $\beta$, 554 amino acids; and $\gamma$, 438 amino acids) have been isolated from cells expressing the single M-CSF gene (Wong et al., 1987, *Science*, 235:1504–1508; Kawasaki et al., 1985, *Science* 230:291–296 (see also U.S. Pat. No. 4,847,201); Ladner et al., 1987, *Embo J.* 6:2693–2698; Cerretti et al., 1988, *Molecular Immunol.*, 25:761–770).

The other CSF molecules have some properties that are similar to M-CSF as described above. G-CSF is more fully described in U.S. Pat. No. 4,810,643 and GM-CSF is more fully described in U.S. Pat. No. 4,438,032, which are both hereby incorporated by reference in their entireties.

G-CSF and GM-CSF occur as monomers, as opposed to M-CSF which is a dimer. G-CSF is know to stimulate granulocyte colony formation and is reported to have a molecular weight of approximately 30,000. GM-CSF is able to stimulate granulocyte and/or macrophage colony formation and has a reported molecular weight of approximately 22,000. Another CSF designated multi-CSF (also known as IL-3) which has been reported to stimulate granulocyte and macrophage formation and has a broad range of proliferative effects on other cells. These CSFs are also included in the invention and are further described in the following references which are hereby incorporated by reference in their entireties: Metcalf, 1986, *Blood* 67:257-267; Clark et al., 1987, *Science*, 236:1229-1237; and Dexter, 1984, *Nature*, 309:746-747.

Naturally occurring interferons (IFNS) are species-specific proteins, often glycoproteins, produced by various cells upon induction with viruses, double-stranded RNAs, other polynucleotides, antigens and mitogens. Interferons exhibit multiple biological activities such as antiviral, antiproliferative, immunomodulatory, and anticellular functions. At least three distinct types of human interferons have been identified and characterized in terms of their anti-viral, anti-growth and activation of natural killer cell (NK) activities. They are produced by leukocytes, lymphocytes, fibroblasts and the immune system and are classified as ($\alpha$, $\gamma$, and $\beta$ interferons, respectively. These are reported to be different proteins coded for by distinct structural genes.

Native human $\beta$-interferon (HuIFN-$\beta$) is generally produced by superinducing human fibroblast cultures with poly-IC (poly-riboinosinic acid and polyribocytidylic acid) and isolating and purifying the HuIFN-$\beta$ thus produced by chromatographic and electrophoretic techniques. Proteins or polypeptides which exhibit native $\beta$-interferon properties may also be produced using recombinant DNA technology by extracting poly-A-rich 12S messenger RNA from vitally induced human cells, synthesizing double-stranded cDNA using the mDNA as a template, introducing the cDNA into an appropriate cloning vector, transforming suitable microorganisms with the vector, harvesting the bacteria and extracting the HIFN-$\beta$ therefrom. Nagola et al. 1980, *Nature*, 284:316; Goeddel et al., 1980, *Nature*, 287:41 1; Yelverton et al., 1981, *Nuc. Acid Res.*, 9:731; Streuki et al., 1981, *PNAS (USA)*, 78:2848; European Patent Application Nos. 28,033 (published May 6, 1981), 321,134 (published Jul. 15, 1981), and 34,307 (published,, Aug. 26, 1981); and Belgian Patent No. 837,379 (issued Jul. 1, 1981) describe various currently used methods for the production of $\beta$-interferon employing recombinant DNA techniques. The expression proteins or polypeptides have been purified and tested and have been found to exhibit properties similar to those of native IFNS. Therefore, bacterially produced IFNs thus appear to have therapeutic use as antiviral and antitumor agents.

Procedures for recovering and purifying bacterially produced IFNs are described in U.S. Pat. Nos. 4,450,103, 4,315,852, 4,343,735, and 4,343,736 (which are hereby incorporated by reference in their entireties); Derynck et al., 1980, *Nature* 287:193-197; and Scandella and Kornberg, 1971, *Biochemistry*, 10:4447.

The human IFN-$\alpha$ genes compose a multigene family sharing 85-95% sequence homology (Goeddel et al., 1981, *Nature*, 290:20-27, and Nagata et al., 1981, *J. Interferon Research*, 1:333-336). Several of the IFN-$\alpha$ genes have been cloned and expressed in *E. coli* (Nagata et al. 1980, *Nature*, 284:316-320; Goeddel et al., 1980, *Nature*, 287:411-415; Yelverton et al., 1981, *Nucleic Acid Research*, 9:731-741; and Streuli, *PNAS (USA)*, 78:2848-2852. The resulting polypeptides have been purified and tested for biological activities associate with partially purified native human IFNs and found to possess similar activities. Accordingly, such polypeptides are potentially useful as antiviral, immunomodulatory, or antiproliferative agents.

Polypeptides having IFN-$\alpha$ activity are also described in U.S. Pat. Nos. 4,801,685 and 4,414,150; EP No. 32,134; Weismann et al., 1982, *UCLA Sym. Mol. Cell Bio.*, 25:295-326; and Pestka, August 1983, *Scientific American* pp. 37-43, which are hereby incorporated by reference in their entireties.

IFN-$\gamma$ is a 146 amino acid polypeptide which generally begins with Cys-Tyr-Cys and ends with Glu. It also has antiproliferative antitumor and immunoregulatory properties. IFN-$\gamma$ is more fully described in Gray et al., 1982, *Nature*, 295:503; U.S. Pat. No. 4,835,256; and EP Nos. 167,852, 196,203, 137,691, 159,714, and 136,694.

Processes for preparing and/or purifying these proteins are shown in the following references: IFN-$\gamma$, European Patent Application Nos. 170,917, 169,907, 136,620, and 137,691; PCT Application No. WO 85/05619; IFN-$\alpha$, U.S. Pat. No. 4,801,685 or European Patent Application No. 32,134; IFN-$\beta$, U.S. Pat. Nos. 4,462,940, 4,530,787, 4,588,585, and 4,737,462 or European Patent Application No. 83,069. All of the above described references are hereby incorporated in their entireties.

Other proteins that can be conjugated to polymers are described as follows. Production of TNF is shown in U.S. Pat. Nos. 4,677,063 and 4,677,064. Lymphotoxin is more fully described in Paul et al., 1988, *Ann. Rev. Micro.*, 6:407-438. IL-1 production is more fully described in Durum et al., 1985, *Ann. Rev. Micro.*, 3:263-287. IL-6 production is more fully described in Kishimoto, 1989, *Blood*, 74:1-10, and Revel, 1989, *Experientia*, 45:549-557. IL-4 production is more fully described in Paul et al., 1988, *Ann. Rev. Micro.*, 6:429-459. Kishimoto et al., 1988, *Ann. Rev. Micro.*, 6:485-512, also describe several of the above proteins.

Figure 2:
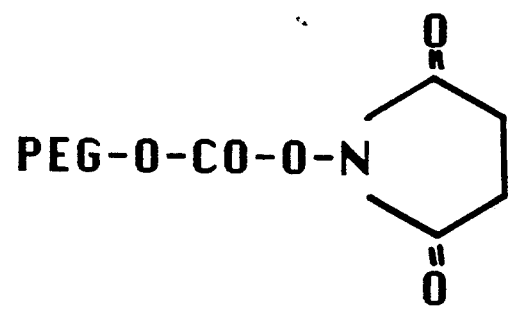
FIG. 2 shows the chemical structure of the activated ester.

The Active Ester:

The present invention involves reacting a polymer, such as PEG, with disuccinimidylcarbonate to form a PEG active ester (see FIG. 2). However, it will be obvious to one skilled in the art that variants of DSC can be employed in the present invention. For example, di, 3, 3'sulfo-succinimidyl carbonate and other acidic alcohols for which chloroforrnate is unstable. After the PEG active ester is formed, it can be reacted with a protein to form a PEG/protein conjugate.

The PEG active ester shown in FIG. 2 can be produced by methods known in the prior art. However, the prior art methods that were used to produce the PEG active ester are unlike the present method. They ar-, disadvantageous because they use unstable reactants (chlorocarbonates of N-hydroxysuccimide) and involve the use of phosgene at the reaction site, which is quite disadvantageous.

Disuccinimidylcarbonate ($C_9H_8N_2O_7$) may be purchased from such companies as Fluka Chemika-Biochemika, etc. It is also called di(N-N'-succinimidyl) carbonate, bis-succinimidyl carbonate, or DSC, and has a molecular weight of about 256. Its chemical structure is shown in FIG. 1.

DSC can be made by reaction of 1 mole of phosgene with 2 moles of N-hydroxysuccininiide under the appropriate reaction conditions shown in the art; it is stable upon storage.

To construct the active PEG ester, PEG-OH is dissolved at room temperature in an appropriate solvent, such as $CHC_3$, or $CH_2C_2$. Preferably, DSC is suspended in $CH_3CN$, for example, and added to the PEG solution at a 30 mole excess or less, more preferably a 20 mole excess or less. Preferably an acylation catalyst is added between 0 and 1 hours later, preferably the catalyst is pyridine or 4-dimethylaminopyridine (DMAP). The mixture is allowed to mix for preferably at least 4 hours, more preferably at least 16 hours. At this point, a precipitate may form. It is removed by filtration and discarded. Filtering devices such as Whatman glass fiber filters (GH/B) are acceptable. The resulting solution contains the PEG active ester as well as unreacted PEG (if any) and catalyst and excess DSC. The PEG active ester is precipitated by adding an ether, preferably diethyl ether. The precipitate can be washed with appropriate solvents such as ether, redissolved and reprecipitated if necessary.

The active ester can be assayed by a standard method for N-hydroxysuccinimide esters, i.e., in 100 mM Tris buffer, pH 8-0. A precisely weighed amount (generally about 50 mg) of active ester is dissolved in 100 nil of Tris buffer and the solution is immediately read in a spectrophotometer at 260 $\lambda$; the molar extinction coefficient for released N-hydroxy-succinimide anion is 8520. By precisely observing the increase of N-hydroxy-succinimide anion liberated in time, one can calculate the half-life of the ester in this solution, as well as total amount of active ester per sample weighed. In this manner I found the amount of active ester to be 91–95% in the samples weighed and the half-life in Tris buffer at ambient temperature to be about 1 minute (temperature was not controlled).

Polymer Protein Conjugation:

After the PEG active ester is formed, it can be conjugated with the protein to produce: PEG-O-CO-NH-Protein.

In the final product, the PEG moiety is bound to the protein by a urethane, also called a carbamate, bond. This bond is relatively stable and will keep PEG conjugated to the protein with little or no hydrolysis under physiological conditions.

The PEG active ester can be conjugated to a protein such as IL-2 in the following manner. The PEG active ester is preferably dissolved in an aqueous solution, such as 10 mM sodium acetate, pH 5.5. The IL-2 concentration is preferably between 0.5 and 10 mg/ml IL-2, more preferably between 1 and 5 mg/ml. The solution has a preferred pH range between 8 and 10, more preferably between 7.5 and 9.5 in a buffer which preferably comprises 0.1M sodium borate or 0.1M EPPS (N- (2-hydroxyethyl) piperazine-N-3-propane sulfonic acid) pH 8.5, (available from Sigma). Other common buffers such as phosphate and Tris can be used. However, those buffers which contain unhindered amines which would react with the active ester should not be employed. The PEG active ester solution is added (at room temperature) to the IL-2 to a molar ratio preferably between 1 and 30 moles of PEG active esters per IL-2, more preferably between 1 and 15 moles of PEG active esters per mole IL-2, and most preferably about 5 moles of PEG active esters per mole IL-2. However, there may be situations in which more PEG molecules should be attached to the subject protein. In that case, the ratio of PEG active ester to protein will need to be increased. Preferably the IL-2 and PEG active ester is allowed to react for between 10 minutes and 24 hours, more preferably between 20–40 minutes. A final yield of between 1 and 3 PEGs per IL-2 is preferred. More preferably, the final conjugate, contains between 2 and 3 PEGs per IL-2.

The conjugates which ar-e produced by this, and prior art methods can have a wide range of PEGs per IL-2. However, a mixture of conjugates having the specific average number of PEGs per IL-2 discussed above are preferred because they can be more bioactive. If desired, these preferred PEG/IL-2 conjugates can be purified from the reaction mixture. There are many purification methods that are known to those of ordinary skill in the art such as size exclusion chromatography, hydrophobic interaction chromatography, ion exchange chromatography, preparative isoelectric focusing, etc. These methods can also be combined; for example, size exclusion chromatography can be combined with ion exchange. Preferably, a size separation method is used, such as size exclusion chromatography which discriminates between molecules based on their hydrodynamic radius. Hydrodynamic radius is defined as the effective molecular radius of a particle in an aqueous environment. A preferable charge separation method is ion exchange chromatography which discriminates between molecules based on differential affinity of charged ions or molecules in solution for inert immobile charged substances. The size exclusion chromatography method and the ion exchange chromatography method are preferably run in the appropriate buffers and under the appropriate conditions. More preferably, the size exclusion chromatography column has the appropriate sieving capacity to size PEG/IL-2 conjugates with a molecular weight range preferably between 5,000 and 1,000,000. Examples of commercial columns are Sephacryl° S-200, S-300, and S-400 HR (high resolution), and Superose 12. More preferably, the ion exchange chromatography column can discriminate between individual species of PEG/IL-2 conjugates ranging in isoelectric point between 4 and 9, most preferably it can discriminate between PEG/IL-2 conjugates which range between 5.5 and 7.5 in isoelectric charge.

Typically, the output from these purification methods, i.e. size exclusion chromatography or ion exchange chromatography, is a UV ($A_{280}$) absorbance profile of the eluted fractions some of which contain the conjugate. To determine which fractions contain the preferred conjugates (among other conjugates), the fractions can be screened against various standards. Preferred screening methods include SDS-PAGE, isoelectric focusing, capillary zone electrophoresis bioactivity, and pharmacokinetics. Once it is known which fraction contains the preferred conjugates, those fractions may be further purified. For example, the polymer/protein conjugate mixture can be contacted with the size exclusion chromatography column, the fractions collected, then run on an SDS-PAGE gel to determine which fractions contain the preferred polymer/protein conjugates (among others). Then, the fractions of interest may be contacted with the ion exchange column, the fractions collected, and analyzed by isoelectric focusing to determine which fractions have the preferred polymer/protein conjugates. Before the PEG/IL-2 conjugate mixture is subjected to chromatography, it may be initially prepared by removing impurities. For example, salts may be removed with preparatory columns, or may be dialyzed against appropriate buffers.

Once the PEG/protein is purified it may be tested for bioactivity using methods known in the art. If the conjugate is PEG/IL-2, for example, a HT-2 cell proliferation assay using the MTT stain is acceptable and is similar to the assay described by Gillis, et al., 1978, *J. Immunol.*, 120:2027-2032.

After the PEG/protein is produced and purified it may be incorporated into a pharmaceutical composition because it is considered therapeutically effective for human and veterinary uses, such as cancer therapy and the treatment of infectious diseases. See U.S. Pat. No. 4,902,502 which is incorporated by reference in its entirety. The PEG/protein can be formulated in a non-toxic, inert, pharmaceutically acceptable aqueous carrier medium, preferably at a pH ranging from 3 to 8, more preferably ranging from 6 to 8. When used for in vivo therapy, the sterile PEG/protein composition will comprise protein dissolved in an aqueous buffer having an acceptable pH upon reconstitution. The PEG/protein can be formulated with a number of excipients such as amino acids, polymers, polyols, sugars, buffers, preservatives, other proteins, etc. Specific examples include: octylphenoxy polyethoxy ethanol compounds; polyethylene glycol monostearate compounds; polyoxyethylene sorbitan fatty acid esters; sucrose; fructose; dextrose; maltose; glucose; dextran; mannitol; sorbitol; inositol; galactitol; xylitol; lactose; trehalose; bovine or human serum albumin; citrate; acetate; Ringer's and Hank's solutions; saline; phosphate; cysteine; arginine; carnitine; alanine; glycine; lysine; valine; leucine; polyvinylpyrrolidone; polyethylene glycol; etc. Preferably this formulation is stable for at least 6 months at 4° C.

The conjugate composition can be parenterally administered to the subject by methods known in the art. This composition may contain other compounds that increase the effectiveness or promote the desirable qualities of the protein. The composition must be safe for administration via the route that is chosen, sterile and effective. To maintain the sterility and to increase the stability of the protein, the composition is lyophilized and reconstituted prior to use.

Preferably, the formulation is suitable for parenteral administration to humans or animals in therapeutically effective amounts. These amounts may be determined by the in vivo efficacy data obtained after preclinical testing. The following test systems are relevant when PEG/IL-2 is the conjugate: T-cell mutagenesis, cytotoxic T-cell induction, natural killer cell augmentation, IFN-$\beta$ induction, enhancement or restoration of cellular immunity (e.g. treatment of immune deficient conditions), and cell mediated anti-tumor activity.

The present process will now be illustrated by reference to the following examples which set forth particularly advantageous embodiments. However, it should be noted that these embodiments are illustrative and are not to be construed as restricting the invention in any way.

EXAMPLE I

PEG Active Ester Preparation

Monomethyl PEG (M-PEG-OH) was reacted with DSC to produce the PEG active ester. The DSC was obtained from Fluka Chemica - Biochemica Company.

3 grams of M-PEG-OH, having an average molecular weight of 6110 (purchased from Union Carbide, West Virginia), was dissolved in approximately 25 ml of $CH_2Cl_2$. A 20 molar excess of DSC (2.5 g) was suspended in 25 ml of $CH_3CN$ and added to the M-PEG-OH solution, followed by 0.4 ml of pyridine and another 1.5 ml pyridine after 30 minutes. The suspension was stirred overnight. The solution did not clarify. The precipitate was removed by filtration using a Whatman glass microfiber filter (GF/B) and discarded. The mother liquor was treated with 400 ml of dry ether. The white precipitate was redissolved (twice) in 40 ml of $CH_2Cl_2$ and reprecipitated twice more with 200 ml of dry ether. The yield was 1.91 g of white powder (92% active ester).

The corresponding synthesis using DMAP as catalyst instead of pyridine was somewhat different, since the original reaction mixture became homogeneous and excess DSC could not be simply filtered off. First, treatment of the reaction mixture with dry ether (450 ml) yielded a gummy precipitate (mostly DSC which was removed), and required additional dry ether (400 ml) to precipitate the PEG derivative. The product was reprecipitated twice from $CH_2Cl_2$-ether solution; the yield was 1.94 g of white powder (95% active ester).

The pyridine catalyzed preparation was 92% active and had a half life of 0.81 minutes. The DMAP catalyzed preparation was 95% active and had a half life of 1.1 minutes.

EXAMPLE II

Assay of PEG-O-CO-NHS

The PEG active ester assay is conducted in 100 mM Tris, pH 8.0, using spectrophotometer readings at 260 $\lambda$; the molar extinction coefficient for N-hydroxysuccinimide anion is 8520.

The active ester of monomethoxy-polyethylene glycol material, showing an average molecular weight of 6321, was weighed out at 58.400 mg, dissolved into Tris buffer and the spectrophotometer readings taken every 30 seconds. The results are as follows:

| Time, Second | Absorbance at 260$\lambda$ |
|---|---|
| 90 | 1.69300 |
| 120 | 1.78330 |
| 150 | 1.83860 |
| 180 | 1.87880 |
| 210 | 1.90810 |
| 240 | 1.93950 |
| 270 | 1.93320 |
| 300 | 1.96280 |

Final absorbance at 30 minutes was 1.99070. From this data the calculated half-life of this ester was 1.1 minute and 95% of the polyethylene glycol molecules were esterified.

EXAMPLE III

PEG/IL-2 Conjugation

The PEG active ester was produced in a manner similar to Example II, and the IL-2 was produced in a manner similar to that described in PCT Patent Publication WO 88/08849, published Nov. 17, 1988. Briefly, *E. coli* was transformed with a plasmed containing the IL-2 gene and the appropriate regulatory sequences. The *E. coli* was induced, the IL-2 was produced, and then recovered by the appropriate separation and purification methods.

An IL-2 solution was made, which contained 100 mM EPPS buffer and 2 mg/ml IL-2 at pH 8.5. Activated PEG esters were added to the IL-2 solution in a molar ratio of approximately 5:1 PEG active esters per IL-2. The solution was stirred at room temperature for 30 minutes. The molar ratio of 12 PEGs per IL-2 was designed to produce a maximum amount of a conjugate having a molar ratio of 2 or 3 PEGs per IL-2. As shown by SDS-PAGE, approximately 60% of the conjugates had a molar ratio of 2 or 3 PEGs per IL-2. A similar result was obtained when borate buffer was used.

EXAMPLE IV

SDS-PAGE was carried out on the crude PEG-IL-2 products (conjugated in EPPS) using BioRad precast 12% gels. HPLC sizing was performed using a Superose 12 column (Pharmacia) in 100 mM $Na_2SO_4$, 10 mM $Na_2HPO_4$, pH 7.0, at 0.5 ml/minute. Prior to HPLC, SDS was removed from the PEG-IL-2 sample by ion exchange, using a Q-Sepharose column. The results showed that the PEG-IL-2 conjugates resolved into two discrete bands on the gels which corresponded to species having 2 and 3 PEGs per IL-2.

EXAMPLE V

Conjugate Purification

For a larger scale purification the conjugates can be concentrated using an Amicon stirred cell fined with a YM 10 membrane. The conjugate concentrate is washed with 50 mM sodium acetate buffer at pH 5.5 to produce a final protein concentration of 35 mg/ml. The conjugate concentrate can be loaded on a Sephacryl® S-200 HR column equilibrated with a 50 mM sodium acetate buffer pH 5.5, and fractions collected. Selected fractions, based on a UV absorbance profile, can be run on reducing 12.5% SDS-PAGE and appropriate pools can be made to select conjugates having a molar ratio of 2 or 3 PEGs per IL-2. Size exclusion HPLC (a Zorbax GF 250 column and a buffer containing 30 mM sodium phosphate at pH 7 and 100 mM sodium sulfate) can be used to confirm that the pools contained predominantly a molar ratio of 2 and 3 PEGs per IL-2.

The present invention has been described with reference to specific embodiments. However, this application is intended to cover those changes and substitutions which may be made by those skilled in the art without departing from the spirit and the scope of the appended claims.

I claim:

1. A method for producing an activated ester of polyethylene glycol (PEG) or a polyoxyethylated polyol, comprising:
   a) contacting PEG or a polyoxyethylated polyol, which has at least one hydroxyl group, with disuccinimidylcarbonate (DSC) under the appropriate reaction conditions to form a PEG or a polyoxyethylated polyol active ester.

2. A method in accordance with claim 1, wherein PEG is activated with the DSC.

3. A method in accordance with claim 2, wherein the molar ratio of DSC to PEG is 30:1 or less.

4. A method in accordance with claim 2, wherein the molar ratio of DSC to PEG is 20:1 or less.

5. A method in accordance with claim 2 further comprising adding a catalyst selected from the group consisting essentially of pyridine or 4-dimethylaminopyridine.

6. A method in accordance with claim 1, wherein the PEG or the polyoxyethylated polyol has a average molecular weight between 1,000 and 40,000.

7. A method in accordance with claim 1, wherein the PEG or the polyoxyethylated polyol has a average molecular weight between 2,000 and 20,000.

8. A method in accordance with claim 1, wherein the PEG or the polyoxyethylated polyol has an average molecular weight between 3,000 and 12,000.

9. A method in accordance with claim 6, wherein the polymer is PEG.

10. A method in accordance with claim 1 further comprising:
    a) contacting the PEG or the polyoxyethylated polyol active ester with a protein under the appropriate reaction conditions to form a PEG or a polyoxyethylated polyol protein conjugate.

11. A method in accordance with claim 10, wherein the PEG or the polyoxyethylated polyol active ester is contacted with the protein in the molar ratio of between 1 and 30 moles active esters to 1 mole protein.

12. A method in accordance with claim 11, wherein the active ester is contacted with the protein in the molar ratio of between 1 and 15 moles active esters to 1 mole protein.

13. A method in accordance with claim 10, wherein the PEG or the polyoxyethylated polyol has a average molecular weight between 1,000 and 40,000.

14. A method in accordance with claim 10, wherein the PEG or the polyoxyethylated polyol has a average molecular weight between 2,000 and 20,000.

15. A method in accordance with claim 10, wherein the PEG or the polyoxyethylated polyol has an average molecular weight between 3,000 and 12,000.

16. A method in accordance with claim 11, wherein the active ester is a PEG active ester.

17. A method in accordance with claim 11, wherein the protein is IL-2.

18. A method in accordance with claim 11, wherein the protein is CSF.

19. A method in accordance with claim 11, wherein the protein is interferon.

20. A method in accordance with claim 17, wherein the PEG active ester is contacted with IL-2 in the molar ratio around 5 moles of PEG esters to 1 mole IL-2.

* * * * *